United States Patent [19]

Baker et al.

[11] 4,203,998
[45] May 20, 1980

[54] FUNGICIDAL USE OF CHLORO-SUBSTITUTED PHENOXY ETHERS

[75] Inventors: Don R. Baker, Orinda; Malcolm B. McClellan, San Jose, both of Calif.

[73] Assignee: Stauffer Chemical Co., Westport, Conn.

[21] Appl. No.: 589,112

[22] Filed: Jun. 23, 1975

Related U.S. Application Data

[63] Continuation of Ser. No. 50,971, Jun. 29, 1970, abandoned, and a continuation-in-part of Ser. No. 657,003, Jul. 31, 1967, abandoned, which is a continuation-in-part of Ser. No. 574,529, Aug. 24, 1966, abandoned.

[51] Int. Cl.$^2$ ............................................. A01N 9/28
[52] U.S. Cl. .................................... 424/283; 424/285
[58] Field of Search ................ 424/283, 285, 340, 341

[56] References Cited

U.S. PATENT DOCUMENTS

| 2,327,338 | 8/1943 | Carswell | 424/340 |
| 2,463,541 | 3/1949 | Houk | 424/341 |
| 2,615,823 | 10/1952 | Lawlor et al. | 424/340 |
| 2,833,829 | 5/1958 | Schrader | 260/613 X |
| 2,870,169 | 1/1959 | Dazzi | 260/347.8 |

OTHER PUBLICATIONS

Chem. Abst., vol. 58, Item 13919f, 1963.
Chem. Abst., vol. 61, Item 15998g, 1964.

*Primary Examiner*—Douglas W. Robinson
*Attorney, Agent, or Firm*—Harry A. Pacini

[57] ABSTRACT

Chloro-substituted phenoxy ethers useful as fungicides. Representative compounds include 2-(2,4-dichlorophenoxy)tetrahydropyran, 2-(2,4,5-trichlorophenoxy)tetrahydropyran and 1-(2,4,5-trichlorophenoxy)-1-isobutoxy ethane.

3 Claims, No Drawings

FUNGICIDAL USE OF CHLORO-SUBSTITUTED PHENOXY ETHERS

This is a continuation, of application Ser. No. 50,971, filed June 29, 1970 now abandoned.

This application is a continuation-in-part of Ser. No. 657,003 filed July 31, 1967 now abandoned, which application was a continuation-in-part of Ser. No. 574,529, filed Aug. 24, 1966, now abandoned.

This invention relates to novel chloro-substituted phenoxy ethers. In another aspect this invention relates to a method of controlling the growth and development of fungi, and more particularly, to a method of effectively imparting fungistatic properties to habitats susceptible to fungus by treatment with certain chloro-substituted phenoxy ethers.

The novel compounds of this invention are represented by the formula

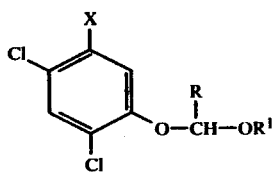

wherein X is chlorine, and jointly R and $R^1$ are a divalent alkylene radical containing 3 to 4 carbon atoms. Compounds which exhibit fungistatic activity in accordance with the present invention include the compounds described and represented by the formula

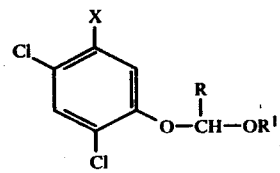

wherein X is selected from the group consisting of hydrogen and chlorine, R is lower alkyl containing from 1 to 4 carbon atoms, inclusive, $R^1$ is alkyl containing 1 to 6 carbon atoms, inclusive, and jointly R and $R^1$ are a divalent alkylene radical containing 3 to 4 carbon atoms.

The compounds of the invention are readily prepared by contacting an appropriate di or tri chloro phenol with a 4-carbon or 5-carbon cyclic α-vinyl ether or an aliphatic α-vinyl ether. The addition reactions to the α-vinyl linkage are generally carried out in the presence of a Lewis-type catalyst, such as naphthalene sulfonic acid. In certain instances when the α-vinyl ether is sufficiently active no catalyst is needed. The reactions proceed readily in the liquid phase. The employment of an inert organic solvent is also useful, aiding in the processing as well as agitation of the reactants. These reactions are usually exothermic although slight warming is employed to initiate the reaction in certain cases. After the reaction is completed the mixture is cooled to room temperature and isolated.

Compounds as defined above are effective fungistats. Incorporation of these compounds and compositions or formulations containing same into the substance or on the surface susceptible of fungus infection retards growth thereof. Representative substances susceptible to fungus growth include cloth, leather, paint, soaps, paper, wood, plastic, oil, and the like. It is contemplated that the compounds of the present invention are particularly useful in soaps, shampoos, and the like for dermal applications since the oral toxicity of certain of these compounds is very low. For example, the acute oral LD-50 of 2-(2,4,5-trichlorophenoxy)tetrahydropyran, which comprises a preferred compound within the scope of the present invention, is in excess of about 4.6 grams-per-kilogram.

For maximum effectiveness the active ingredients of the present invention are admixed in fungistatically effective amounts with an inert adjuvant. In order to provide formulations particularly adapted for ready and efficient application to the material to be treated, such formulations comprise those of both the liquid and solid types as well as the "aerosol" type formulations. Applications are directly to the substance to be protected from fungus growth. In the pure state the active ingredient may be too potent in some applications to have practical utility. For most effective protection it is preferred to apply the materials in intimate contact but thoroughly dispersed on or in the surface to be protected. Therefore, the active ingredients have incorporated therewith a relatively inert agent or adjuvant as a dispersing medium, utilizing methods well-known to those skilled in the art.

Suitable formulations of the compounds of this invention comprise the above defined active ingredients and a suitable material as an adjuvant therefor. Fungistat compositions are advantageously formulated by first preparing a solution thereof in an organic solvent and then adding the resulting solution to water or other carrier. If necessary an emulsifying agent is employed. The compositions can be incorporated into solid carriers such as clay, talc, pumice, soap, and the like. Also, they can be dissolved in liquefied gases such as fluorochloroethanes or methyl chloride and applied from aerosol bombs containing the solution. It should be noted that suitable formulations may also include adhesive agents, indicators, and other microbiocidal ingredients. Other ingredients can be supplenentary insecticides, fungicides, bactericides, nematocides or selective herbicides.

Since the amount of active agent of the present invention which is employed will vary with the fungistatic effect sought, the utility of the treated material, the type and dimensions of the material treated, it is evident that no rigid limits can be set forth on the quantity required. Determination of the optimum effective concentration for a specific application is readily conducted by routine procedures, as will be apparent to those skilled in the art.

The compounds of the present invention are special value in application, for example, to textiles to impart to the textile protection against mildew or other fungus or bacterial attack. The compounds are conveniently applied to textiles by dissolving the compound in acetone and diluting this solution with water to the desired concentration. The textile is then rinsed in the solution and allowed to air dry. Effective amounts of the compounds in the range of 1 part per million to 5 percent can be deposited upon the textile in this manner. Because of the low concentrations in which the compounds are effective as microbiostats, the compounds can be applied to light colored or white fabrics with no impairment of the color of the textile.

The following example illustrates the preparation of the compounds of the present invention.

EXAMPLE

Preparation of 2-(2,4,5-trichlorophenoxy) tetrahydropyran 2,4,5-trichlorophenol (9.85 g., 0.05 moles) and dihydropyran (9.1 ml., 0.10 moles) are mixed in 100 ml. of benzene as a solvent. Upon addition of 1.0 g. of naphthalene sulfonic acid, as catalyst, the reaction is exothermic and the solution turns a light purple color. The reaction mixture is cooled to room temperature and allowed to stand for about one-half hour. The reaction mixture is washed with dilute sodium carbonate solution and the color turns to a light orange. The solution is dried over magnesium sulfate and then the solvent is evaporated in vacuo to yield 14.5 g. of an orange oil, $n_D^{30} = 1.5408$.

Representative examples of compounds within the scope present invention are:
2-(2,4-dichlorophenoxy) tetrahydropyran
2-(2,4,5-trichlorophenoxy) tetrahydropyran
2-(2,4-dichlorophenoxy) tetrahydrofuran
2-(2,4,5-trichlorophenoxy) tetrahydrofuran
1-(2,4-dichlorophenoxy)-1-(isobutoxy) ethane
1-(2,4,5-trichlorophenoxy)-1-(isobutoxy) ethane
1-(2,4-dichlorophenoxy)-1-(propoxy) ethane
1-(2,4,5-dichlorophenoxy)-1-(propoxy) ethane
1-(2,4-dichlorophenoxy)-1-(ethoxy) ethane
1-(2,4,5-trichlorophenoxy)-1-(ethoxy) ethane
1-(2,4-dichlorophenoxy)-1-(hexoxy) ethane
1-(2,4,5-trichlorophenoxy)-1-(hexoxy) ethane
1-(2,4-dichlorophenoxy)-1-(ethoxy) butane
1-(2,4,5-trichlorophenoxy)-1-(ethoxy) butane
1-(2,4-dichlorophenoxy)-1-(butoxy) butane
1-(2,4,5-trichlorophenoxy)-1-(butoxy) butane
1-(2,4-dichlorophenoxy)-1-(ethoxy) pentane
1-(2,4,5-trichlorophenoxy)-1-(ethoxy) pentane
1-(2,4-dichlorophenoxy)-1-(butoxy) pentane
1-(2,4,5-trichlorophenoxy)-1-(butoxy) pentane.

In Vitro Vial Tests

Compounds are tested to determine the microbiostatic efficacy when in contact with growing fungi or bacteria in an artificial medium. For each candidate compound four 1-ounce vials are partially filled; two with malt broth and two with nutrient broth. The compound to be tested is placed in the vials at the desired concentration (expressed in parts per million). The vials are inoculated with water suspensions of spores of the desired fungi, *Aspergillus niger* and *Penicillium* sp. and cells of the bacteria, *Escherichia coli* and *Staphylococcus aureus* (one organism per vial). The vials are then sealed and held for one week, after which time the growth of the organisms is observed and noted. The tests are repeated using lower concentrations of the candidate compounds to determine the lowest concentration that can be used and still offer some control of the growth of the organism. The following table shows the results of the in Vitro tests.

TABLE

| | In Vitro Test Lowest Effective Concentration (ppm) | | | |
|---|---|---|---|---|
| Compound | *Aspergillus niger* | *Penicillium* sp. | *Escherichia coli* | *Staphylococcus aureus* |
| 2-(2,4-dichlorophenoxy)tetrahydropyran | 50 | (25) | >50 | — |
| 2-(2,4,5-trichlorophenoxy)tetrahydropyran | 5* | 5* | >50 | >50 |
| 1-(2,4,5-trichlorophenoxy)-1-(isobutoxy) ethane | 5 | 5 | >50 | >50 |
| 1-(2,4,5-trichlorophenoxy)-1-(ethoxy) ethane | 50 | 50 | >50 | 50 |

*indicates lowest rate tested
()indicates partial control at this concentration
>indicates no activity up to stated level Further fungicide In Vitro tests are performed with 2-(2,4,5-trichlorophenoxy) tetrahydropyran against fungi in an artificial medium. The compound is diluted with melted nutrient agar and also melted Emmons agar to give concentrations of 5 ppm and 1 ppm. The melted agar is allowed to solidify in Petri dishes. The nutrient agar plates are inoculated with *Aspergillus niger* cells and the Emmons agar plates are inoculated with *Pullularia pullulans* cells. The plates are held at room temperature for one week after which time the results are observed and noted. The *A. niger* is completely controlled at 5 ppm and partially controlled at 1 ppm. The *Pullularia pullulans* is partially controlled at 5 ppm.

Textile Treatment Test

In order to test the applicability of the present method of inhibiting microbiological development, cotton fabric is treated therewith and the resulting inhibiting effect investigated. The test is performed according to the following procedure.

The compound 2-(2,4,5-trichlorophenoxy) tetrahydropyran is dissolved in sufficient acetone to give a 1% solution. From this solution is taken 0.5 ml. and this is added to 500 ml. of tap water to give a resulting concentration of 10 ppm of the test compound in water. The solution of water and test chemical is agitated for a short period of time. Following the preparation of the rinsing solution the fabric samples are added. Four one-inch square pieces of 8 oz. white cotton duck are used as the test fabric. The fabric samples are agitated gently for five minutes in the test solution. All of the cloth samples are then removed and allowed to air dry until yet damp.

Sterile, melted and cooled nutrient agar is inoculated with *Aspergillus niger* by streaking the agar plates with cells of the organism. One piece of damp-dry treated fabric sample is placed on the inoculated agar and incubated at room temperature for three days. After the incubation period, a zone of 1 mm forms around the treated fabric sample in which no fungi are growing. The fabric sample contains thereon an effective amount of microbiostatic agent exhibited by a zone of inhibition comprising an area surrounding the samples wherein fungicidal growth is not observed.

Various changes and modifications may be made without departing from the spirit and scope of the invention described herein as will be apparent to those skilled in the art to which it pertains. It is accordingly intended that the present invention shall only be limited by the scope of the appended claims.

What is claimed is:

1. The method of controlling the growth of fungi comprising applying to the habitat of said fungi a fungistatically effective amount of a compound having the formula

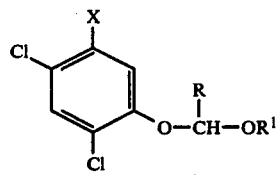

wherein X is selected from the group consisting of hydrogen and chlorine, and jointly R and $R^1$ are a divalent alkylene radical containing 3 to 4 carbon atoms.

2. The method according to claim 1 wherein X is hydrogen and R and $R^1$ jointly are tetramethylene.

3. The method according to claim 1 wherein X is chlorine, and R and $R^1$ jointly are tetramethylene.

* * * * *